United States Patent
Finka et al.

(10) Patent No.: US 11,667,887 B2
(45) Date of Patent: Jun. 6, 2023

(54) METHOD OF PRODUCING A RECOMBINANT PROTEIN

(71) Applicant: Glaxo Group Limited, Middlesex (GB)

(72) Inventors: Gary Brian Finka, Stevenage (GB); Michael Hoare, London (GB); Mark Uden, Stevenage (GB); Ioannis Voulgaris, London (GB)

(73) Assignee: Glaxo Group Limited, Middlesex (GB)

( * ) Notice: Subject to any disclaimer, the term of this patent is extended or adjusted under 35 U.S.C. 154(b) by 432 days.

(21) Appl. No.: 15/574,214

(22) PCT Filed: May 13, 2016

(86) PCT No.: PCT/EP2016/060807
§ 371 (c)(1),
(2) Date: Nov. 15, 2017

(87) PCT Pub. No.: WO2016/184794
PCT Pub. Date: Nov. 24, 2016

(65) Prior Publication Data
US 2018/0135008 A1    May 17, 2018

Related U.S. Application Data

(60) Provisional application No. 62/161,939, filed on May 15, 2015.

(51) Int. Cl.
| | | |
|---|---|---|
| C12N 1/38 | (2006.01) | |
| C12P 21/02 | (2006.01) | |
| C07K 16/00 | (2006.01) | |
| C07K 16/28 | (2006.01) | |
| C07K 1/14 | (2006.01) | |

(52) U.S. Cl.
CPC ............... *C12N 1/38* (2013.01); *C07K 16/00* (2013.01); *C07K 16/2878* (2013.01); *C12P 21/02* (2013.01); *C07K 1/145* (2013.01); *C07K 2317/14* (2013.01); *C07K 2317/569* (2013.01)

(58) Field of Classification Search
None
See application file for complete search history.

(56) References Cited

U.S. PATENT DOCUMENTS

2007/0031930 A1\*  2/2007  Gehant ................. C07K 16/22
                                                                    435/488

FOREIGN PATENT DOCUMENTS

| WO | WO 2006/055264 A1 | 5/2006 | |
|---|---|---|---|
| WO | WO-2006055264 A1 * | 5/2006 | ........... A61K 9/0019 |
| WO | WO 2014/118220 A1 | 8/2014 | |

OTHER PUBLICATIONS

Burgess R.R., Methods of Enzymology, vol. 463, pp. 331-342 (2009).*
Krober et al., Chemical Engineering Technology, vol. 33, No. 6, pp. 941-959 (2010).*
Burgess R.R., Methods of Enzymology, vol. 463, pp. 331-342 (2009) (of record). (Year: 2009).*
Helander et al., Microbiology, vol. 143, pp. 3193-3199 (1997) (Year: 1997).*
Chatel et al., Biotechnology and Bioengineering, vol. 111, No. 5, pp. 913-924 (electronically available Dec. 28, 2013). (Year: 2013).*
Helander et al., Microbiology, vol. 143, pp. 3193-3199 (1997) (of record). (Year: 1997).*
Chatel et al., Biotechnology and Bioengineering, vol. 111, No. 5, pp. 913-924 (electronically available Dec. 28, 2013) (of record). (Year: 2013).*
Krober et al., Chemical Engineering Technology, vol. 33, No. 6, pp. 941-959 (2010) (of record). (Year: 2010).*

\* cited by examiner

*Primary Examiner* — Paul J Holland
(74) *Attorney, Agent, or Firm* — Carly A. Shanahan

(57) ABSTRACT

The present invention relates to a method of producing a recombinant protein in a host cell comprising adding Polyethyleneimine (PEI) during cell culture. Addition of PEI to the cell culture as a fermentation enhancer can result in reducing the viscosity of the cell culture, and/or increasing the extracellular concentration of the recombinant protein, and/or reducing the duration of cell culture to the point of harvest or protein recovery.

14 Claims, 6 Drawing Sheets

Specification includes a Sequence Listing.

METHOD OF PRODUCING A RECOMBINANT PROTEIN

This application is a 371 of International Application No. PCT/EP2016/060807, filed May 13, 2016, which claims benefit of U.S. Provisional 62/161,939, filed on May 15, 2015, all of which are incorporated herein in their entireties.

The present invention relates to a method of producing a recombinant protein in a host cell comprising adding Polyethyleneimine (PEI) during cell culture. Addition of PEI to the cell culture as a fermentation enhancer can result in reducing the viscosity of the cell culture, and/or increasing the extracellular concentration of the recombinant protein, and/or reducing the duration of cell culture to the point of harvest or protein recovery.

BACKGROUND OF THE INVENTION

Large-scale and cost-effective manufacture, recovery and purification of recombinant proteins are important challenges for the biotechnology industry.

*E. coli* and Chinese Hamster Ovary (CHO) host cells are two of the most widely used organisms for the production of recombinant proteins. Considerations during production include host cell growth and expression of recombinant protein, protein titre, protein location (e.g. intracellular, extracellular, periplasmic, etc.), and selective recovery and purification from the final location of the recombinant protein. Balancing and optimising these different factors is not straightforward.

Accordingly, there is a need for improved methods of producing, recovering and purifying recombinant proteins.

SUMMARY OF THE INVENTION

The present invention provides a method of producing a recombinant protein in a host cell comprising adding PEI during cell culture.

Also provided is a method of releasing recombinant protein expressed by a host cell culture comprising adding PEI during cell culture.

Also provided is a method of reducing the viscosity of a cell culture expressing a recombinant protein, comprising adding PEI during cell culture.

Also provided is a method of increasing the extracellular concentration of a recombinant protein expressed by the cell culture, comprising adding PEI during cell culture.

Also provided is a method of reducing the length of time to harvest of a cell culture expressing a recombinant protein, comprising adding PEI during cell culture.

Also provided is a pharmaceutical composition comprising a recombinant protein obtained using the methods described herein.

Also provided is the use of PEI as a cell culture enhancer of a host cell culture expressing a recombinant protein.

Also provided is the use of PEI as a release agent during cell culture to increase extracellular recombinant protein titre expressed by the cells.

DESCRIPTION OF THE FIGURES

FIG. 3: Effect of cell culture supplements EDTA, EDTA-Urea, and Tween™20 on dAb (DOM01010) production and relative extracellular concentrations of dAb and DNA. Time profiles of A—dry cell weight (DCW), B—capacitance at 1000 KHz C—carbon dioxide evolution rate (CER), D—DNA release to the extracellular space E—extracellular dAb concentration, F—intracellular dAb concentration and G—total dAb concentration, and H—Parity plot comparing release into extracellular environment of both dAb product and DNA for the control culture, cultures treated with EDTA 125 mM at 5 ml/l/h to final [EDTA] of 18 mM, treated with EDTA 125 mM urea 7.5M at 5 ml/l/h to final [EDTA] of 18 mM and [Urea] of 1M, and Tween™20 incrementally over 23 h (done in a controlled way to avoid excessive foaming) at final concentration of 20 ml/l. The line at 35 h process time signifies the beginning of the EDTA and EDTA-urea feed. For FIG. 3H, closed points are for % extracellular dAb release against maximum level achieved in EDTA or EDTA-urea fermentations; open points are for % dAb release against maximum as obtained in control.

FIG. 6: The effect of PEI treatment (0.09 g/l/h) on extracellular antigen binding protein product. FIGS. 6A, B and C for 5 h, 25 h and 50 h post-PEI addition respectively; and soluble DNA concentration in FIGS. 6D, E and F for 5 h, 25 h and 50 h post-PEI addition respectively; for four different recombinant antigen binding proteins (including DOM0101/TNFR1-dAb), MWs of the antigen binding proteins range from 13 to 25 kDa. The relative extracellular product is the proportional increase in released antigen binding proteins (=antigen binding protein released using PEI as proportion of antigen binding protein released at harvest without PEI). Application of PEI started at ~4 h after the induction of the recombinant antigen binding protein product.

DETAILED DESCRIPTION

The present disclosure involves the realisation that a more cost effective and efficient method of producing, recovering and purifying recombinant protein is possible by using polyethyleneimine (PEI) in the fermentation, i.e. adding PEI to the culture medium during cell culture.

Cell culture as used in the present disclosure is given its broadest meaning, namely the bulk growth of cells in a growth medium. "Fermenting" and "culturing" as used herein means bulk growing the cells in a growth medium. The terms "fermenting" and "culturing" are used interchangeably herein. The cells are not in the resting phase. The exponential phase is a period characterized by cell doubling, therefore bulk growth. The number of new cells appearing per unit time increases significantly and is proportional to the existing population. The stationary phase is where the growth rate and death rate of the cells is equal often due to a growth-limiting factor such as the depletion of an essential nutrient, and/or the formation of an inhibitory product such as an organic acid. To maintain a constant biomass in the stationary phase and therefore bulk growth, the cells need to continue to grow. In an embodiment, PEI is added during cell culture whilst the cells are actively growing and expressing recombinant protein i.e. the cells are not resting. In an embodiment, the PEI addition is prior to harvest.

The terms extracellular medium, culture broth, supernatant, extracellular environment, extracellular space, culture medium, and fermentation medium, are all used herein to describe the external environment of the cells during cell culture and at the point of harvest.

The term harvest is used herein to mean the end of fermentation. Harvest may be at any time point during fermentation that is considered sufficient to end the fermentation process and recover the recombinant protein being expressed, i.e. protein recovery begins at the point of harvest. The time of harvest may depend on the optimum concentration of recombinant protein in the supernatant. The recombinant protein may be recovered and purified directly from the extracellular medium of the cell culture at harvest. Alternatively, the cells may be separated away from the extracellular medium prior to recovery and purification of the product from the extracellular medium.

Polyethyleneimine (PEI) is a cationic polymer comprised of primary, secondary and tertiary amines, $(C_2H_5N)_n$. PEI is not used herein as a transfection agent, nor is PEI used herein as an attachment factor for cell culture.

Accordingly, the methods herein describe the use of PEI as a cell culture enhancer (or cell culture supplement) which results in multiple advantages, including one or more of the following: reduced the viscosity of the cell culture; and/or increased extracellular recombinant protein titre; and/or location of the product in the supernatant at an earlier time-point; and/or reducing the length of time to harvest the cell culture; and/or a lower level of impurity (for example, DNA, HCP) content in the supernatant, and/or simpler recovery and downstream processing. Thus, PEI is used in the methods herein as a fermentation (or cell culture) enhancer. PEI is added to the cell culture as a cell culture supplement (or agent). In one aspect, we describe the use of PEI as a cell culture supplement prior to harvest of a host cell culture expressing a recombinant protein to reduce the viscosity of the cell culture. In another aspect, we describe the use of PEI as a cell culture supplement prior to harvest of a cell culture expressing a recombinant protein to increase the extracellular concentration of the recombinant protein. In a further aspect, we describe the use of PEI as a cell culture supplement prior to harvest of a cell culture expressing a recombinant protein to reduce the length of time to harvest.

PEI can be used herein as a membrane permeabilising agent (also referred to as a release agent; the terms are used interchangeably) to increase the extracellular recombinant protein titre. PEI as a release agent can be used when the recombinant protein is targeted to the periplasm of a Gram negative bacterium, such as *E. Coli*, to release periplasmically expressed/located protein into the extracellular medium.

The methods herein describe the use of PEI as a cell culture enhancer which can result in greater quantities of recombinant protein product in the supernatant, and/or location of the product in the supernatant at an earlier time-point. Thus the point of harvest may be changed to an earlier time-point because sufficient recombinant protein is located in the extracellular medium in the presence of PEI.

The recombinant protein concentration in the extracellular medium may be at least 2-fold greater in the presence of PEI. For example, the recombinant protein concentration is at least 3-fold, or at least 4-fold, or at least 5-fold, or at least 6-fold, or at least 7-fold, or at least 8-fold, or at least 9-fold, or at least 10-fold, greater in the presence of PEI. This can be at any time-point during fermentation, or at the point of harvest.

The time-point of harvest may be at least 5 hours earlier in the presence of PEI than in the absence of PEI without significantly impacting product yield. For example, harvest may occur at least 10 hours, at least 15 hours, at least 20 hours, at least 25 hours, at least 30 hours, at least 35 hours, at least 40 hours, at least 45 hours, or at least 50 hours, earlier in the presence of PEI than in the absence of PEI without significantly impacting product yield. Product yield is determined by measuring the recombinant protein concentration in the presence of PEI and in the absence of PEI. No significant impact on product yield results when an increased product yield is observed at an earlier time-point in the presence of PEI, compared with a significantly similar product yield at a later time-point in the absence of PEI.

PEI may be added as a single or multiple bulk additions or as a continuous addition during all or some of the fermentation. For example, PEI may be added prior to harvest. PEI may be added at the time of induction of expression of the recombinant protein or after inducing expression of the recombinant protein. PEI may be added at any time from induction of expression of the recombinant protein to about 30 minutes prior to harvest.

PEI may be added to the cell culture at least 30 minutes prior to harvest. PEI may be added to the cell culture at least 1 hour, or at least 2, or at least 5, or at least 10, or at least 15, or at least 20, or at least 25, or at least 30, or at least 40, or at least 50 hours prior to harvest.

PEI may be added to the cell culture at any time between induction and harvest in an inducible cell expression system. PEI may be added at the time of induction of expression of the recombinant protein. Alternatively, PEI may be added at least 1 hour, or at least 2, or at least 5, or at least 10, or at least 15, or at least 20, or at least 25; or at least 30; or at least 40; or at least 50; or at least 60 hours after inducing expression of the recombinant protein.

PEI may be present in the cell culture for at least 30 minutes. PEI may be present in the cell culture for between 1-60 hours, or between 1-50 hours, or between 1-40 hours.

PEI may be added continuously during cell culture. This is similar to the "feeding" or "feed rate" of media, nutrients, and growth factors, that may be continuously added to the cell culture. In an embodiment PEI is added to the cell culture at a rate of about 0.01 to 1 g/L/hr, or 0.03 to 0.3 g/L/hr, or 0.05 to 0.2 g/L/hr. In another embodiment the PEI is added at a rate of 0.09 g/L/hr or 0.16 g/L/hr. In an embodiment PEI is added to the cell culture at a rate of about 0.1 to 10 ml/L/hr, or 0.5 to 5 ml/L/hr, or 1 to 3 ml/L/hr. In another embodiment the PEI is added at a rate of 1.5 ml/L/hr or 2.5 ml/L/hr.

PEI may be added to the cell culture as a bulk addition. This may be a single bulk addition or multiple bulk additions.

The total amount of PEI added to the cell culture via continuous or bulk additions may be about 10 g/L or less. Thus at the point of harvest (the end of the fermentation) PEI may have a concentration in the cell culture of about 10 g/L or less. In another embodiment, the total amount of PEI added to the cell culture is about 5 g/L, or 4 g/L, or 3 g/L, or 2.5 g/L, or 2 g/L or less. In mammalian cells, the total PEI concentration in the cell culture may be between 0.025 to 250 μg/ml.

PEI used in methods of the disclosure can be branched or linear. In an embodiment the PEI is branched.

The molecular weight (MW) of the PEI for use in the methods of the disclosure is between about 600 Da and about 1000 kDa. In an embodiment the PEI MW is between 50 and 1000 kDa. In an embodiment, the PEI MW is about 750 kDa. In an embodiment the PEI is branched and has a MW of 50 to 1000 kDa. Alternatively, the PEI is branched and has a MW of about 750 kDa.

In an embodiment the amount of soluble DNA present in the extracellular environment in the presence of PEI is reduced compared to in the absence of PEI. In an embodiment the amount of DNA present in the extracellular environment in the presence of PEI is at least 2-fold less than in the absence of PEI. For example, the DNA concentration is at least 3-fold, or at least 4 fold, or at least 5-fold, or at least 6-fold less in the presence of PEI. This can be at any time-point during fermentation, or at the point of harvest.

In an embodiment the soluble DNA concentration remaining in the supernatant after addition of PEI is less than 600 mg/L, less than 500 mg/L, less than 400 mg/L, less than 300 mg/L or less than 250 mg/L. In an embodiment the DNA concentration in the harvest is about 250 mg/L.

The disclosure also provides a method of reducing the viscosity of a cell culture by culturing the cells in the presence of PEI. In an embodiment the viscosity in the presence of PEI is reduced by at least 2-fold than in the absence of PEI. For example, the viscosity is reduced by at least 3-fold, or at least 4 fold, or at least 5-fold, or at least 6-fold less in the presence of PEI. This can be at any time-point during fermentation, or at the point of harvest.

Thus PEI acts as a fermentation enhancer to reduce the viscosity and/or reduce the DNA concentration in the cell culture (i) during fermentation, and/or (ii) at the point of harvest. This may result in many advantages including one or more of: lower impurity content in the extracellular medium, more efficient handling, simpler recovery of the cells/product at the point of harvest, and improved downstream processing.

"About" as used herein when referring to a measurable value such as an amount, a molecular weight, a temporal duration, and the like, is meant to encompass variations of ±1%, ±0.75%, ±0.5%, ±0.25%, ±0.2%, and ±0.1% from the specified value, as such variations are appropriate to perform the methods described.

Recombinant Protein

The recombinant protein may comprise an antigen binding protein, for example a monoclonal antibody, an antibody fragment, or a domain antibody (dAb).

The recombinant protein may comprise a viral protein, a bacterial toxin, a bacterial toxoid, or a cancer antigen.

As used herein a "recombinant protein" refers to any protein and/or polypeptide that can be administered to a mammal to elicit a biological or medical response of a tissue, system, animal or human. The recombinant protein may elicit more than one biological or medical response.

Furthermore, the term "therapeutically effective amount" means any amount which, as compared to a corresponding subject who has not received such amount, results in, but is not limited to, healing, prevention, or amelioration of a disease, disorder, or side effect, or a decrease in the rate of advancement of a disease or disorder. The term also includes within its scope amounts effective to enhance normal physiological function as well as amounts effective to cause a physiological function in a patient which enhances or aids in the therapeutic effect of a second pharmaceutical agent.

The term "antigen binding protein" as used herein refers to antibodies, antibody fragments and other protein constructs, such as domains, which are capable of binding to an antigen.

The term "antibody" is used herein in the broadest sense to refer to molecules with an immunoglobulin-like domain. As used herein, "immunoglobulin-like domain" refers to a family of polypeptides which retain the immunoglobulin fold characteristic of antibody molecules, which contain two b-sheets and, usually, a conserved disulphide bond. This family includes monoclonal (for example IgG, IgM, IgA, IgD or IgE), recombinant, polyclonal, chimeric, humanised, bispecific and heteroconjugate antibodies; a single variable domain, a domain antibody, antigen binding fragments, immunologically effective fragments, Fab, F(ab')2, Fv, disulphide linked Fv, single chain Fv, diabodies, TANDABS™, etc (for a summary of alternative "antibody" formats see Holliger and Hudson, Nature Biotechnology, 2005, Vol 23, No. 9, 1126-1136).

The phrase "single variable domain" refers to an antigen binding protein variable domain (for example, VH, VHH, VL) that specifically binds an antigen or epitope independently of a different variable region or domain. A "domain antibody" or "dAb" may be considered the same as a "single variable domain".

As used herein "domain" refers to a folded protein structure which retains its tertiary structure independently of the rest of the protein. Generally, domains are responsible for discrete functional properties of proteins and in many cases may be added, removed or transferred to other proteins without loss of function of the remainder of the protein and/or of the domain. By single antibody variable domain or immunoglobulin single variable domain is meant a folded polypeptide domain comprising sequences characteristic of an antibody variable domain. It therefore includes complete antibody variable domains and modified variable domains, for example in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain.

A domain antibody can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains).

The domain antibody may be a human antibody variable domain. The dAb™ may be of human origin. In other words, the dAb™ may be based on a human Ig framework sequence.

As used herein, the term "antigen binding site" refers to a site on an antigen binding protein which is capable of specifically binding to an antigen, this may be a single domain, or it may be paired VH/VL domains as can be found on a standard antibody. Single-chain Fv (ScFv) domains can also provide antigen-binding sites.

The antigen binding protein may comprise additional antigen binding sites for different antigens. For example, the antigen binding protein may have specificity for more than one antigen, for example two antigens, or for three antigens, or for four antigens.

The antigen binding protein may consist of, or consist essentially of, an Fc region of an antibody, or a part thereof, linked at each end, directly or indirectly (for example, via a linker sequence) to a binding domain. Such an antigen binding protein may comprise two binding domains separated by an Fc region, or part thereof. By separated is meant that the binding domains are not directly linked to one another, and may be located at opposite ends (C and N terminus) of an Fc region, or any other scaffold region.

The antigen binding protein may comprise two scaffold regions each bound to two binding domains, for example at the N and C termini of each scaffold region, either directly or indirectly via a linker. Each binding domain may bind to a different antigen.

The antigen binding protein may take the protein scaffold format of a mAbdAb. "mAbdAb" and "dAbmAb" are used interchangeably, and are intended to have the same meaning as used herein. Such antigen-binding proteins comprise a protein scaffold, for example an Ig scaffold such as IgG, for example a monoclonal antibody, which is linked to a further binding domain, for example a domain antibody. A mAbdAb has at least two antigen binding sites, at least one of which is from a domain antibody, and at least one is from a paired VH/VL domain.

Domain antibodies can exist and bind to target in monomeric or multimeric (e.g. dimeric) forms, and can be used in combination with other molecules for formatting and targeting approaches. For example, an antigen-binding protein having multiple domains can be made in which one of the domains binds to serum proteins such as albumin. Domain antibodies that bind serum albumin (AlbudAbs) are described, for example, in WO05/118642 and can provide the domain fusion partner an extended serum half-life in its own right.

dAbs may also be conjugated to other molecules, for instance in the form of a dAb-conjugate or a dAb-fusion with other molecules e.g. a drug, another protein, an antibody molecule or an antibody fragment. For example a dAb™ can be present as a formatted dAb™, e.g. the dAb™ can be present as a dAb-Fc fusion or conjugate as described in for example WO 2008/149148. Alternatively, the formatted dAb™ can be present as a mAbdAb, as described in WO 2009/068649. The dAb™ may be present as a fusion or conjugate with half life extending proteins or polypeptides, for example, a further dAb™ which binds to serum albumin (AlbudAb), or to a half life extending chemical moiety such as polyethyleneglygol (PEG). The dAb™ may be present as a fusion or conjugate with further therapeutic or active molecules.

As used herein, "drug" refers to any compound (for example, a small organic molecule, a nucleic acid, a polypeptide) that can be administered to an individual to produce a beneficial therapeutic or diagnostic effect through binding to and/or altering the function of a biological target molecule in the individual. The target molecule can be an endogenous target molecule encoded by the individual's genome (e.g., an enzyme, receptor, growth factor, cytokine encoded by the individual's genome) or an exogenous target molecule encoded by the genome of a pathogen. The drug may be a dAb™ or mAb.

A "dAb conjugate" refers to a composition comprising a dAb™ to which a drug is chemically conjugated by means of a covalent or noncovalent linkage. Preferably, the dAb™ and the drug are covalently bonded. Such covalent linkage could be through a peptide bond or other means such as via a modified side chain. The noncovalent bonding may be direct (e.g., electrostatic interaction, hydrophobic interaction) or indirect (e.g., through noncovalent binding of complementary binding partners (e.g., biotin and avidin), wherein one partner is covalently bonded to drug and the complementary binding partner is covalently bonded to the dAb™). When complementary binding partners are employed, one of the binding partners can be covalently bonded to the drug directly or through a suitable linker moiety, and the complementary binding partner can be covalently bonded to the dAb™ directly or through a suitable linker moiety.

As used herein, "dAb fusion" refers to a fusion protein that comprises a dAb™ and a polypeptide drug (which could be a polypeptide, a dAb™ or a mAb). The dAb™ and the polypeptide drug are present as discrete parts (moieties) of a single continuous polypeptide chain.

Thus the methods of the disclosure may be applied to one or more of: a therapeutic protein, a monoclonal antibody (mAb), a domain antibody (dAb™), a dAb™ conjugate, a dAb™ fusion, a mAbdAb, or any other antigen binding protein described herein.

In an embodiment, the antigen binding protein is a dAb™ which interferes with TNFα signalling. In an embodiment, the dAb™ neutralises TNFα. In an embodiment, the dAb™ specifically binds to TNFα or a TNFα receptor. In an embodiment, the dAb™ specifically binds TNFR1. In an embodiment, the antigen binding protein is VH dAb™ (anti-TNFR1/DOM0101) of SEQ ID NO:1 (DOM0101); or SEQ ID NO:3 (DOM0101 C-terminal alanine-extended.

Expression of Protein: Host Cell

Suitable host cells include mammalian cells such as CHO (e.g. CHOK1 and CHO-DG44), PerC6; and microbial cells such as Gram-negative bacteria for example *Escherichia coli* (e.g. W3110, and BL21), *Pseudomonas*, and *Salmonella*. In a specific embodiment the host cell is *Escherichia Coli*. In an embodiment the *E. coli* strain is W3110.

A vector comprising a recombinant nucleic acid molecule encoding the recombinant protein is also described herein. Such vectors are employed to genetically engineer cells to express the desired protein product. The vector may be an expression vector comprising one or more expression control elements or sequences that are operably linked to the recombinant nucleic acid. Examples of vectors include plasmids and phagemids.

Suitable expression vectors can contain a number of components, for example, an origin of replication, a selectable marker gene, one or more expression control elements, such as a transcription control element (e.g. promoter, enhancer, terminator) and/or one or more translation signals, a signal sequence or leader sequence. Expression control elements and a signal sequence, if present, can be provided by the vector or other source. For example, the transcriptional and/or translational control sequences of a cloned nucleic acid encoding an antibody chain can be used to direct expression.

A promoter can be provided for expression in a desired cell. Promoters can be constitutive or inducible. For example, a promoter can be operably linked to a nucleic acid encoding an antibody, antibody chain or portion thereof, such that it directs transcription of the nucleic acid. A variety of suitable promoters for Gram negative bacteria (e.g., lac, tac, trp, phoA, lambdapL, T3, T7 (T7A1, T7A2, T7A3) promoters for *E. coli*) may be used. Operator sequences which may be employed include lac, gal, deo and gln. One or more perfect palindrome operator sequences may be employed. In an embodiment expression of the recombinant protein of the disclosure is under the control of an inducible promoter. For example, *E. coli* lac, tac, and trc promoters are inducible with lactose or the non-hydrolyzable lactose analogue, isopropyl-β-D-1-thiogalactopyranoside (IPTG) and the phoA, trp and araBAD promoters are inducible by phosphate, tryptophan and L-arabinose respectively.

The term 'inducing expression' as used herein refers to the point at which induction is initiated, by for example, the addition of an inducer or a change in temperature where induction is temperature dependent. The term 'post-induction' is used herein to describe the elapsed time following the point at which induction is initiated.

In addition, expression vectors typically comprise a selectable marker for selection of cells carrying the vector, and, in the case of a replicable expression vector, an origin of replication. Genes encoding products which confer antibiotic or drug resistance are common selectable markers and may be used (e.g. lactamase gene (ampicillin resistance), Tet gene for tetracycline resistance). Dihydrofolate reductase marker genes permit selection with methotrexate in a variety of cells.

An expression vector as described in WO2007/088371 (for example pAVE037, pAVE007, or pAVE011) may be used to express the protein. In an embodiment, the vector is pAVE011. Alternatively, a vector such as pJExpress401 may be used to express the protein.

Example alternative expression vectors and methodologies (e.g. for use with CHO, PerC6 etc) are also known.

The host cell comprises the recombinant nucleic acid molecule or vector described above.

Host cell cultures of the present disclosure may be cultured in any medium that supports the host cell growth and expression of the recombinant protein. Such media are well known to those skilled in the art.

Protein Targeting

Although expression of a recombinant protein takes place in the cytoplasm, the final location of the recombinant protein may be cytoplasmic, periplasmic or extracellular depending on the nature of the recombinant protein, the host cell used and the fermentation conditions used.

The use of PEI in the present invention may be with respect to a recombinant protein that is targeted to (i) the periplasm of the cell, or (ii) the extracellular medium, by a leader sequence. The recombinant protein may be directed via a leader sequence to the extracellular medium (e.g. in mammalian cells) or to the periplasm (e.g. in Gram negative bacterium).

In mammalian cells, a secretory leader sequence is used to direct the recombinant protein to the extracellular medium. In Gram-negative bacteria, some secreted proteins are exported across the inner and outer membranes in a single step via the type I, type III, type IV or type VI secretion pathways, whereas other proteins are first exported into the periplasm via the universal Sec or Tat pathways and then translocated across the outer membrane mainly via the type II or type V machinery. The type II system involves a two-step process in which a premature protein containing a Sec leader sequence is exported to the periplasm using the Sec pathway. The leader sequence is removed by proteolysis resulting in a mature, processed protein being present in the periplasm and whether or not the protein is secreted to the culture medium highly depends on the characteristics of leader sequence, protein, cell and culture conditions. Also in the case of cell lysis (autolysis) it can be assumed that the majority of the protein in the culture medium originates from the periplasm and therefore is processed. The recombinant protein may be actively secreted into the culture medium via the leader sequence; or passively from the periplasm to the culture medium via other cellular pathways known in the art.

Processing of the leader sequence includes cleavage and removal of the leader sequence from the protein. However, some amino acids of the leader sequence are known to remain at the N-terminus of the protein, such that the leader sequence is not properly processed. The leader sequence may be 90% or more processed, such that 10% or less of the sequence remains at the N-terminus of the protein. The leader sequence may be at least 91, 92, 93, 94, 95, 96, 97, 98, or 99% processed. The leader sequence may about 100% processed, such that none remains at the N-terminus of the protein following passage through the secretory pathway of the cell.

The leader sequence may be a mammalian or human leader sequence; or a periplasmic targeting signal sequence, e.g. an N-terminal periplasmic targeting sequence. Signal sequences to direct proteins to the periplasm or extracellular environment are known in the art. For example, a MalE signal sequence is used. Alternatively, a PelB or OmpA signal sequence is used. In an embodiment the signal sequence is OmpA.

Harvest

Harvest is the end of fermentation. Harvest may be at any time point during fermentation that is considered sufficient to end the fermentation process and recover the recombinant protein being expressed. Harvest may occur between 10 and 60 hours post induction of the cell broth to express the recombinant protein. For example, harvest may occur between 15 and 50 hours post induction. At harvest, the solid content of the microbial cell population may be between 5-30% Wet Cell Weight (WCW). For mammalian cell cultures (e.g. CHO, PerC6, etc) recombinant protein harvest may typically occur between 8 and 500 hours, due to slower division rates as compared to *E. Coli*.

The fermentor volume may be:

(i) about 10,000 litres; about 5,000 litres; about 2,000 litres; about 1,000 litres; about 500 litres; about 125 litres; about 50 litres; about 20 litres; about 10 litres; about 5 litres; or (ii) between 5 and 10,000 litres; between 10 and 5,000 litres; between 20 and 2,000 litres; between 50 and 1,000 litres.

The harvest may comprise cells that have naturally lysed, also known as auto-lysis. For example, 1-50% of the cells in the harvest may have undergone autolysis. Alternatively, 20-50%; or 30-50%; or 40-50% of the cells in the harvest have autolysed. Alternatively, 10% or more; 20% or more; 30% or more; 40% or more; or 50% or more of the cells in the harvest have autolysed. Autolysis may be indirectly determined by DNA concentration in a clarified harvest, or by capacitance, as described in the Examples.

Harvest may include the optional step of emptying the fermentor of the cells and extracellular media (i.e. the cell culture or broth).

Optional Pre-Treatment of Harvest

Dependent on host cell and recombinant protein, the pre-treatment of the harvest is a method of conditioning the harvest. This step may be carried out in the fermentor, or after the harvest has been removed from the fermentor. Pre-treatment includes: thermally, mechanically or chemically lysing the harvest (for example by homogenisation, freeze-thaw, lysis); and periplasmic extraction. At least one periplasmic extract may be extracted using methods known in the art. Alternatively if sufficient product is already present in the extracellular environment then such pre-treatment may not be required.

Clarification

Clarification is the process to remove solid particulates. Clarification can lower the burden on subsequent chromatographic steps during purification. Typical clarification steps comprise a settling step—also known as sedimentation (e.g. by gravity), and/or a centrifugation step, and/or a filtration step.

The centrifugation step may be continuous centrifugation (e.g. with a continuous feed zone). The centrifuge may in itself be operating "batch" or "intermittently" or "continuously" with respect to discharging the solids. For example, a tubular bowl centrifuge may be used as the continuous centrifugation step.

Purification of the Recombinant Protein

The recombinant protein may be recovered directly from the culture medium. Recovery of the recombinant protein is followed by purification to ensure adequate purity of the recombinant protein. One or more chromatography steps may be used in purification, for example one or more chromatography resins; and/or one or more filtration steps. For example affinity chromatography using resins such as protein A or L may be used to purify the recombinant protein. Alternatively, or in addition to, an ion-exchange resin such as a cation-exchange may be used to purify the recombinant protein.

EXAMPLES

Example 1: Materials and Methods

E. coli Expressin System

The E. coli W3110 strain with plasmid pAVE011 harbouring a TNFR1 dAb (DOM0101, SEQ ID NO:1), a VH domain antibody domain of approximately 13.1 kDa molecular weight, with OmpA leader sequence for secretion to the periplasm, was used. [E. coli W3110-pAVE011-ompA-DOM0101, Genotype: E. coli (F− mcrA mcrB IN(rrnD-rrnE)1 lambda].

Cultivation and Bioreactor Settings

E. coli cells were stored in glycerol (20%, v/v) at −80° C. To prepare the inoculum for the bioreactor experiments, 1 ml of glycerol stock was inoculated into each 1000 ml baffled flask (UltraYield Flask, Thomson Instrument Company, Kent, UK) containing 400 ml of vLB inoculation medium (vLB Lennox: select soytone 10 g/l, yeast extract 5 g/L, NaCl 5 g/l, at pH 7.0). The flasks were grown in a rotary-shaking incubator at 220 rpm and at 37° C. until $OD_{600}$ reached 1. The same inoculum was used for each set of bioreactor experiments to avoid seed culture variability.

The parallel 8-bioreactor system had 11 working volume reactors (SR1000DLL bioreactor, vessel diameter 100 mm, aspect ratio 2.4:1), overhead driven double Rushton 6-blade impellers (46 mm dia, DASGIP AG, Julich, Germany).

Bioreactors were inoculated at 1:50 volume ratio so as to yield an initial cell density equivalent to $OD_{600}$=0.02.

The E. coli cells were cultured in a complex medium containing glycerol as the main carbon source, yeast extract and soytone. The pH was kept at 7.0±0.05 by automatic addition of 25% (v/v) $NH_4OH$ and 2M $H_3PO_4$. The temperature was maintained at 30° C. before induction and after induction it was reduced to 26° C. The Dissolved Oxygen (DO) set point was set at 30±5%, and this was automatically controlled by a cascade system which increased sequentially impeller speed (400-1600 rpm) then gas flow rate (1 vvm-2 vvm) (vvm=volume per volume per minute) and then oxygen content in the gas (21-100%), when DO fell below the set point to seek to maintain the minimum DO level.

After the consumption of glycerol a DO spike was observed, at which point a glycerol feed (714 g/l) containing yeast extract (50 g/l) was initiated. The rate of feed addition was 3.6 ml/l/h unless otherwise stated.

For example 4: the feed rates after inductions were 3, 3.6, 4.2 and 4.8 ml/l/h.

For example 5: The continuous addition of 125 mM EDTA (pH 7) and 125 mM EDTA 7 M Urea (pH 7) was initiated at around 15 h post-induction at flow rate of 5 ml/h. Tween™20 addition was initiated at 15 h post-induction and done incrementally over 23 h (done in a controlled way to avoid foaming) to a final concentration of 20 ml/l For example 6: The PEI used was 750 kDa branched (purchased from BASF—Cat No 11736).

The addition of the bulk amount of PEI took place at 23 h post induction (40 ml of 6.25% w/v PEI) leading to a final concentration of PEI in the reactor of 0.25% (w/v). The continuous addition of PEI initiated at 15 h post-induction at rates of 1.5 ml/l/h which corresponds to 0.09 g/l/h (low in FIG. 4) and 2.5 ml/l/h which corresponds to 0.16 g/l/h (high in FIG. 4), (this resulted in a concentration of PEI in fermentation after the end of the fermentation of around 3 and 5 g/l respectively).

For example 7: Harvest material of a control culture as described in example 3, Tween™20, EDTA treated, EDTA—urea treated as described in example 5 and low feed addition of PEI (0.09 g/l/h) as described in example 6 were analysed for extracellular titre but also for contaminants such as Endotoxin, HCP and DNA in the culture supernatant using expressed as per gram of extracellular product. Endotoxin, HCP and DNA was determined as described below (analytical methods).

For example 8: 25 kDa PEI (Aldrich 408727), with the same continuous low feed administration (0.09 g/l/h) as the 750 kDa PEI was applied.

dAb DOM0101 production was induced when the biomass concentration had reached a level corresponding to OD600=80±2, where IPTG was added at a final concentration in the reactor of 250 μM.

Real time values of pH, dissolved oxygen, agitation speed, temperature, air-flow rate, oxygen percentage, oxygen uptake rate, carbon dioxide evolution rate during fermentations were recorded automatically by the bioreactor software (DASGIP Control, Julich, Germany).

All the fermentation treatments were run in duplicates; with each set of experiments run at the same time using the same inoculum. The error bars in the figures represent the standard deviation between at least two replicate bioreactors.

Analytical Methods

The dAb product concentration was measured using a protein A affinity chromatography method. The concentration of product in samples under investigation was analysed using protein A chromatography (HPLC Agilent 1200, Agilent Technologies UK Ltd, West Lothian, UK, fitted with a 1 mL HiTrap MabSelectR Xtra, GE Healthcare Life Sciences, Buckinghamshire, UK). Loading and equilibration were performed using a 0.1 M PBS buffer at pH 7.2. Samples were diluted appropriately in equilibration buffer and filtered using 0.22 μm PVDF syringe filter. Elution was performed using a 20 mM HCl. The amount of product eluted was measured by recording the absorbance at 220 nm. Product peak areas were automatically integrated (Empower, Waters, Milford, USA).

Regarding the intracellular dAb concentration 1 ml of withdrawn culture was centrifuged at 24200×g for 10 min and the cell culture supernatant recovered. The pellet was then re-suspended in 1 ml final volume with 50 mM Tris pH 8, subjected to 4 freeze-thaw cycles (freezing in dry ice followed by incubation in a dry bath for 5 minutes at 37° C.) and 2 freeze-sonication cycles (freezing in dry ice followed by sonication for 15 minutes) using a sonication bath (Camsonix C275, Elma Electronic GmbH, Singen, Germany). The sonicated samples were centrifuged at 24200×g for 10 min and the cell lysate recovered and tested for titre as described above.

The viscosity measurements were carried out using a cup-and-bob rheometer (Brookfield DV-2+ viscometer fitted with spindle 40, Brookfield Engineering Laboratories, MA), exposing 0.5 ml of cell broth to shear rates of 37.5 to 1500 $s^{-1}$ in seven increments with 30 s hold at each increment. Both increasing and decreasing shear sweeps were performed. Temperature was maintained at 23° C. in the viscometer using a cooling water circuit.

The concentration of the double stranded DNA in the extracellular environment was determined using a Qubit 2.0 Fluorometer (Invitrogen, Carlsbad, Calif., USA). 10 μl of appropriately diluted culture supernatant were added in 190 μl Qubit working solution (containing Quant-i dsDNA BR reagent 1:200 in Quant-iT™ dsDNA BR buffer). The tubes were vortexed and the absorbance was measured after exactly 2 min. The same procedure was applied for the two pre-diluted DNA standards at concentration of 0 and 100 ng/μl.

The growth of the culture was measured both as optical density at 600 nm and gravimetrically as dry cell weight (DCW). 1 ml samples were placed into pre-weighed Eppendorfs, and then spun down in a mini-centrifuge at 24200×g for 3 min, the supernatant was discarded and the recovered pellets were re-suspended and washed twice in distilled water and then dried to constant weight in an oven at 105° C. for 24 h. The Eppendorfs were then weighed again and the difference between the final weight and the empty Eppendorfs taken as the DCW.

The capacitance of the culture was measured online at 1000 KHz using Aber probes (Aber Instruments, Aberystwyth, UK) connected via an amplifier to a detector.

The endotoxin levels of the appropriately diluted harvest samples were measured using a commercial portable test system with disposable cartridges containing Limulus Amebocyte Lysate (LAL) following manufacturer's instructions (Charles Rivers Laboratories, USA).

The concentration of the host cell proteins (HCP) in the broth supernatant was measured using an *E. coli* anti-HCP sandwich ELISA method.

Example 2 DNA Concentration and Viscosity

Figure 1:
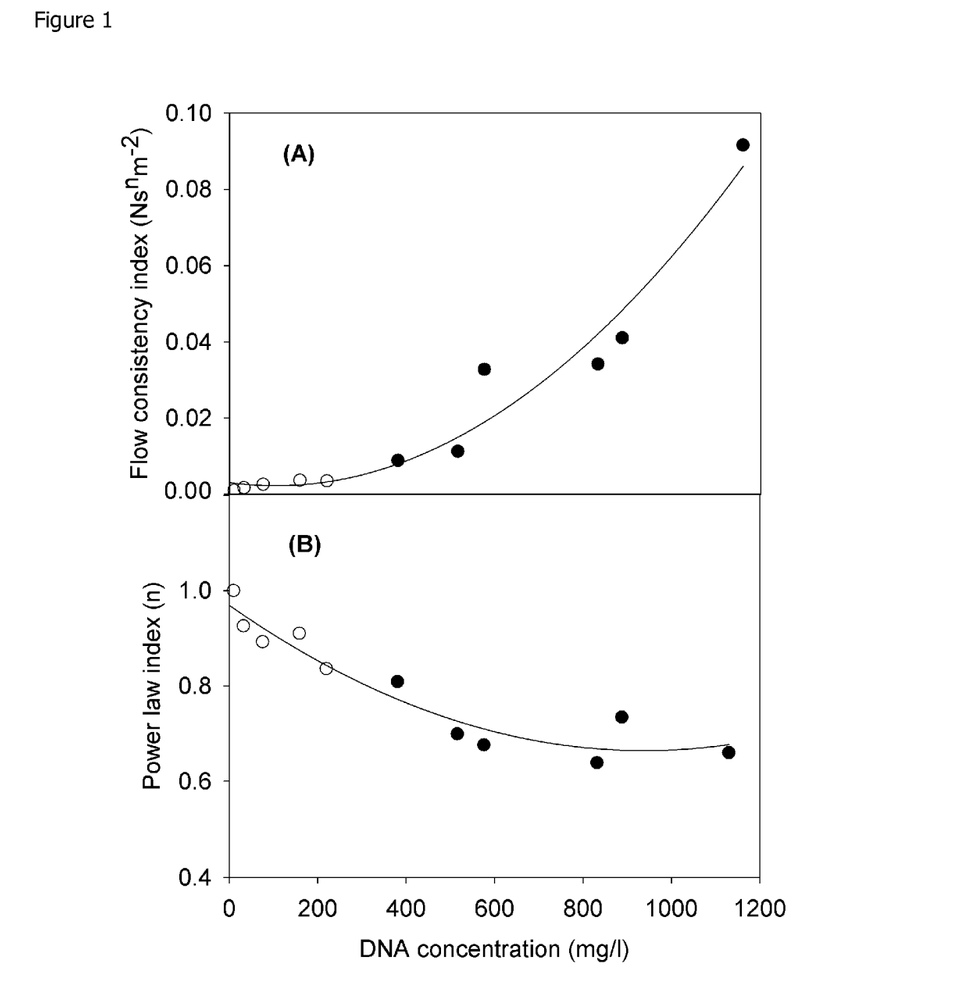
FIG. 1: Rheological properties of *E. coli* fermentation broths as a function of extracellular DNA concentration. (○) pre-induction 0-20 h, cell concentration 0 to 30 g dwt/l; (•) post-induction 20-65 h, cell concentration 30 to 40 g dwt/l. The rheological data is for power law fits, $\tau=k\gamma^n$, ($R^2=0.99$), $\gamma=37$ to $1200$ s$^{-1}$ for 30 s sweeps of both increasing and decreasing shear (no significant difference is observed in values of shear stress between the sweeps). For [DNA]> 1000 mg/ml some samples appeared to exhibit a high apparent yield stress and did not shear. Temperature 23° C.

FIG. 1 characterises the rheological properties of a range of suspensions, including lysed cell broths, as a function of the soluble DNA concentration. All solutions show characteristic pseudoplastic flow behaviour which is time independent and fully reversible. Power law expressions adequately describe the data obtained and the consistency index (equivalent to the apparent viscosity at shear rate 1 $s^{-1}$) gives an indication of the challenge which will be faced when trying to clarify by centrifugation. A consistency index of ~0.03 N $s^n$ $m^{-2}$ obtained at a DNA concentration of 600 mg/l is taken as the limit defining challenging centrifugation.

Example 3 Cell Viability: Capacitance and Dry Cell Weight

Figure 2:
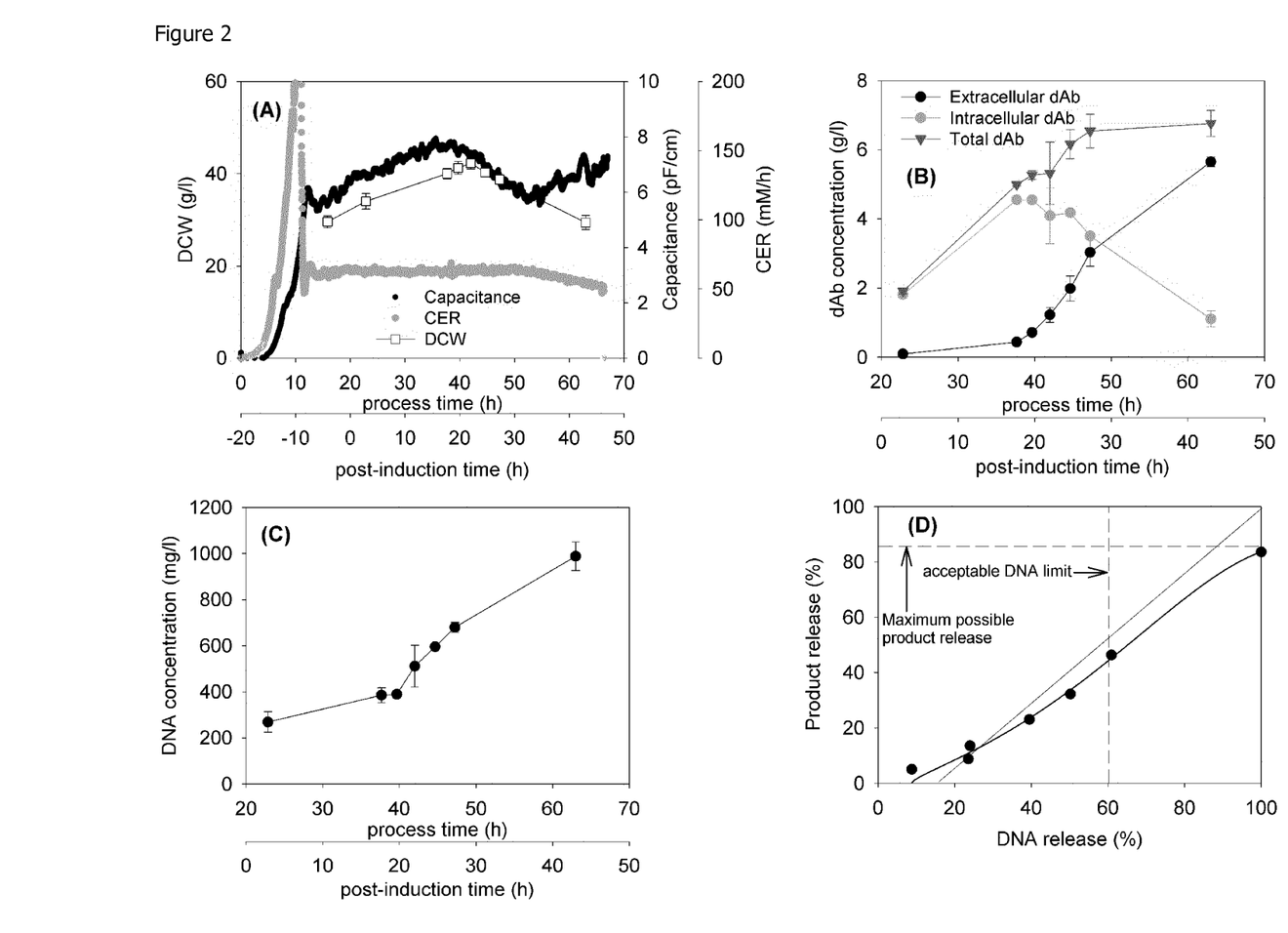
FIG. 2: Production of DOM0101 (dAb) by fermentation and construction of parity plot relating dAb and DNA release. A—Profile of dry cell weight (DCW), capacitance and carbon dioxide evolution rate (CER); B—Profiles of extracellular, intracellular and total dAb; C—Profiles of DNA release to the extracellular space; D—Parity plot comparing release into extracellular environment of dAb and DNA. 100% DNA release=0.031*maximum cell DCW. Construction: parity line (-) is line of equal dAb and DNA release from induction (0% dAb, 17% DNA); the DNA release boundary ( - - - ) refers to the upper limit beyond which the rheological proteins of the broth are such that centrifugation is deemed to be overly challenging.

FIG. 2 provides an example of the standard fermentation used in this study. The post-induction time is used to follow fermentation progression. Intact cell concentration as recorded by capacitance, peaks at 15 h; this is followed soon after by a peak in dry cell weight and a drop in cell respiration (lower CER) at ~30 h (FIG. 2A). This profile is matched by the onset of a significant rise in extracellular domain antibody (dAb) and parallel reduction in intracellular dAb at 15 h and the attainment of a maximum level of total dAb at 30 h (FIG. 2B). The release of DNA (FIG. 2C) increases sharply at the onset of a reduction in DCW and appears to parallel the release of dAb except for an initial high level of DNA present at the onset of induction.

A parity plot (FIG. 2D) follows dAb release with DNA release. The parity line follows the release of dAb and DNA from the initial value at induction to the maximum available on complete disruption of whole cells and cell ghosts. The maximum values are by measurement of dAb and by estimation for DNA by estimation from the maximum cell dry weight; this is due to difficulties in release of all DNA in an intact form for measurement. An acceptable DNA release boundary of 60% is drawn in; this is based on an analysis of the rheology data of lysed suspensions (FIG. 1) showing that DNA levels greater than ~600 mg/l in the broth will lead to poor clarification under typical process-scale centrifugation conditions and also, by observation, evidence of poor mixing e.g. by the appearance of large air bubbles. At this DNA release limit only ~40% of the dAb has been released and the challenge is to find ways of moving above the parity line to achieve high dAb recovery with acceptable limited DNA release.

Example 4 Feed Rate

The effect of changing the carbon source feed rate after induction and the resulting balance of dAb to nucleic acid release was explored. The data for this Example is not shown in the Figures, but is described herein. The range of feed rates chosen was based on a high-end value to avoid excess glycerol accumulation and a low end value below which fermentation exceeds 50 h post-induction. Higher feed rates appear to result initially in small (DCW basis) or no (capacitance basis) increases in biomass levels and then earlier lysis and ultimately lower biomass levels. The CER values reflect the increased biomass activity (up to 20 h) and the earlier onset of lysis as the feed rate is increased. As before the DNA release reflects the extent of cell lysis. The final total, intracellular and extracellular dAb levels are largely unaffected by the choice of feed rate but the higher rates of dAb production at greater feed rates reflects the higher biomass activity, and the earlier release into the extracellular space at greater feed rates reflects the earlier onset of cell lysis. The resultant parity plot shows that the greater the feed rate the higher the extent of release of dAb compared to DNA. The improvement achieved will increase dAb yield from ~35% to ~58% for 60% DNA release; there is no improvement if the target is near complete recovery of dAb. Therefore, there is a need to explore ways to change the relationship between dAb and DNA release during fermentation if opportunities are to be realised for earlier harvest and direct recovery of dAb without further pretreatment.

Example 5 Cell Culture Supplement Part A: EDTA, Urea, Tween™20

EDTA, Urea and Tween™ can be used at harvest to increase protein recovery from host cells. Here we investigated their use during cell culture to investigate any impact on the extracellular concentration of recombinant protein. EDTA can permeabilise cell membranes and is toxic to cells. Urea can impact membrane integrity and is toxic to cells. Tween™ can permeabilise cell membranes and causes foaming of cell cultures.

Figure 3:
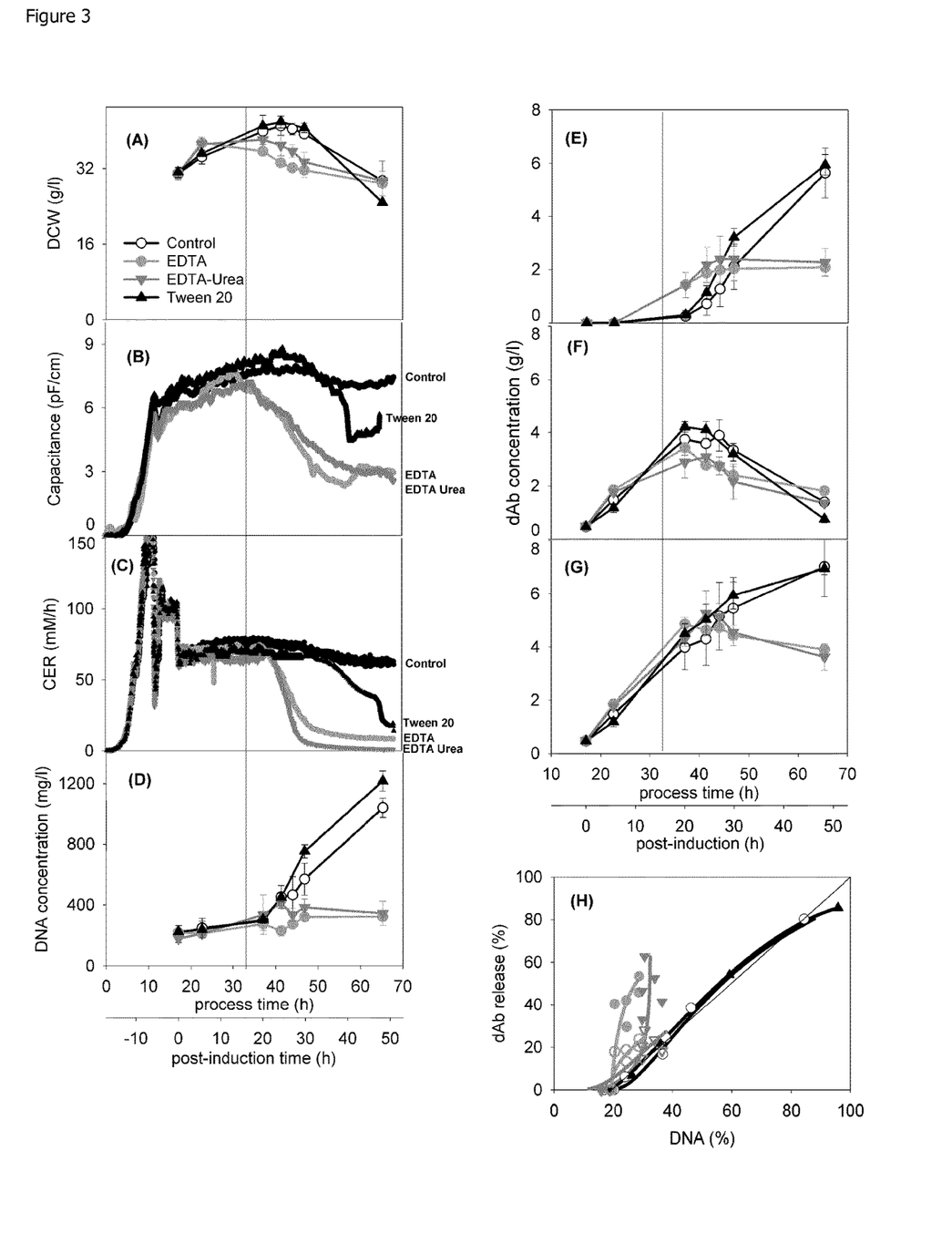

The use of EDTA, Urea and Tween™ was explored in FIG. 3. The concentrations used are based on laboratory-based investigations of ranges of final concentrations of 15 to 75 mM EDTA, 0.5 to 2 M urea and 10 to 20 ml/l Tween™20 (results not shown here). The use of EDTA or EDTA-urea results in a decrease in biomass as evidenced by lower values of dry cell weight (FIG. 3A) and capacitance (FIG. 3B) and reduced CER values (FIG. 3C). The resultant effect is low released DNA levels and total dAb levels (FIGS. 3D & G) but with a significant proportion of the dAb appearing extracellularly (FIG. 3E) evidently as a result of the increased cell wall permeabilisation. As a result there is an overall ~3-fold increase in the ratio of the final dAb to the final DNA release. This improvement is largely due to the reduced dAb titres and indeed recalibration of dAb release against the level of dAb formed in the control brings all the EDTA and EDTA-urea data points back to the parity line.

The use of Tween™ resulted in an earlier onset than the control in loss of active biomass (FIGS. 3A-C) but little difference in the released DNA of dAb profiles (FIG. 3D-G) resulting in no improvement in the ratio of dAb to DNA release (FIG. 3H). Also high levels of foaming were experienced. These strategies were not pursued further as the small scale screening trials indicated little room for improvement with these particular reagents.

Example 6 Cell Culture Supplement Part B: PEI

The use of PEI to help process harvested fermentation broths is known (WO2014118220). Here we are concerned with the use of PEI during the fermentation itself and the impact on live cells. PEI can permeabilise cell membranes and can display antimicrobial activity and cytotoxicity. The results presented here show that surprisingly, PEI seems to have a negligible effect on cell viability.

Figure 4:
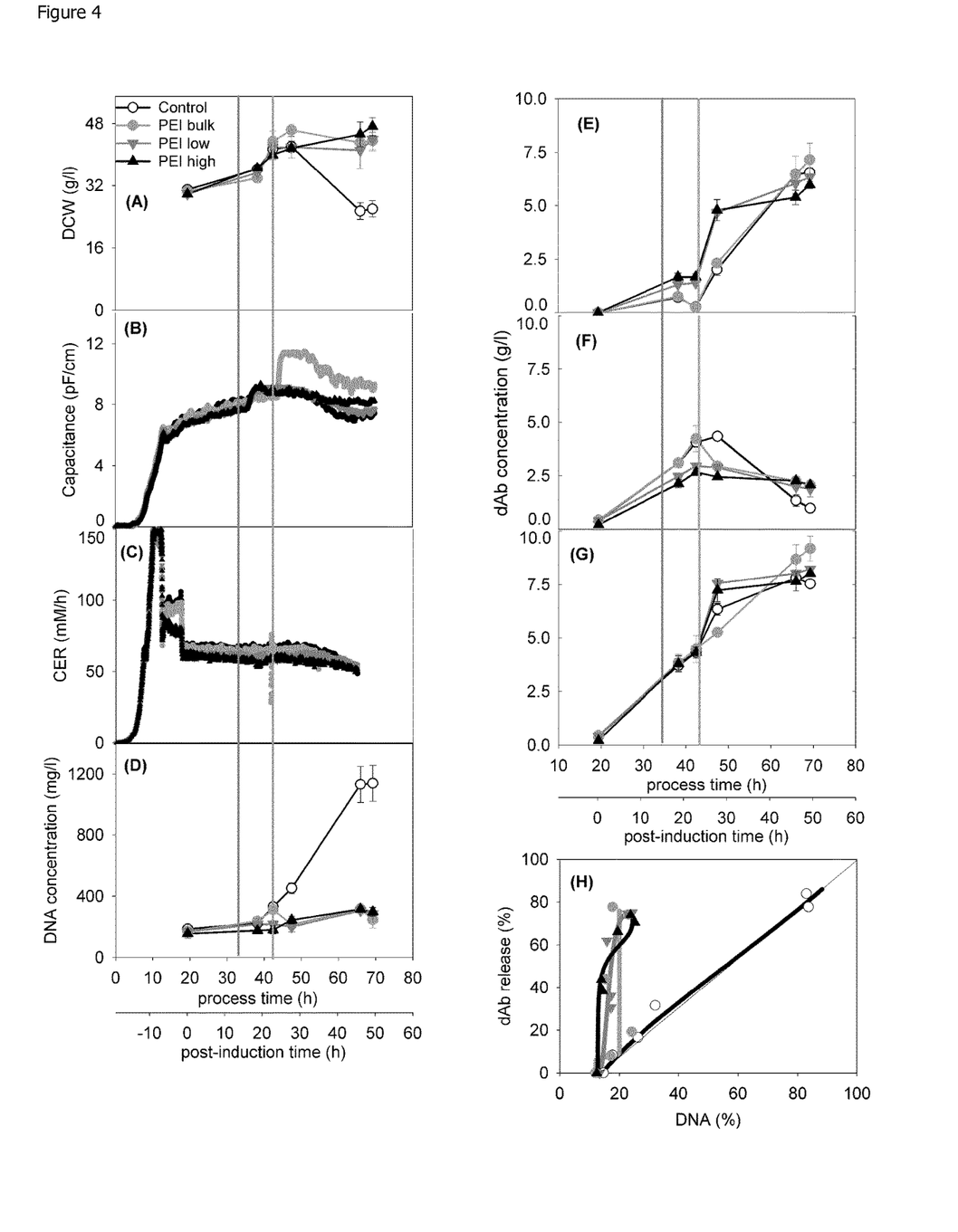
FIG. 4: Effect of cell culture supplement PEI on dAb (DOM0101) production and relative extracellular concentrations of dAb and DNA. Time profiles of A—dry cell weight (DCW), B—capacitance at 1000 KHz, C—carbon dioxide evolution rate (CER), D—DNA release to the extracellular space, E—extracellular dAb concentration, F—intracellular dAb concentration and G-total dAb concentration, and H—Parity plot comparing release into extracellular environment of both dAb product and DNA for the control culture, cultures treated with PEI to a final concentration of around 5 g/l, added as a bulk amount, at a low and high feed rate (0.09 g/l/h and 0.16 g/l/h respectively). The vertical lines at 35 h and 42 h process time signify the onset of the PEI bulk additions and PEI continuous additions respectively.

The addition of a bulk amount of PEI increased the dry cell weight of the culture significantly compared to the control culture. Similarly, in the culture where there was a gradual continuous addition of PEI, significantly higher DCW until the end of the process was observed (see FIG. 4A). While the control culture dropped sharply after 47.5 h, the PEI continuous culture retained DCW close to 42 g/l, and the culture with the bulk addition of PEI retained levels at around 45 g/l. Interestingly, a similar effect was observed in the capacitance readings, where after the addition of the PEI solution there was an abrupt increase in the readings (FIG. 4B). This was especially obvious when bulk addition of PEI took place (the capacitance reading increased from 8.6 pF/cm to 11.5 pF/cm). The respiratory data shows that the PEI treated cultures followed identical profiles to the control culture and they were not affected by the PEI additions (FIG. 4C). The CER was maintained at around 65 mM/h for all of the cultures during the production phase and started decreasing only after 60 h process time.

The extracellular titre profile for the bulk added PEI culture was similar to the control, while the continuous addition of PEI cultures exhibited significantly higher extracellular dAb concentrations from the time of the start of the feed until the end where all cultures reached approximately the same amount of product in the culture supernatant (around 6.5 g/l, see FIG. 4E). For example at 47.5 h process time the continuous PEI addition cultures had an extracellular dAb concentration of 4.7 g/l while the control and bulk PEI added cultures only had 2 g/l and 2.2 g/l respectively. FIG. 4F shows that the intracellular product concentration was lower for the culture with continuous addition of PEI, which corresponds to the increased extracellular product concentration i.e. the cells become more leaky due to the earlier addition of PEI when added in the continuous mode. The total amount of product produced was similar for all of the cultures and ranged from 8.5 to 9.2 g/l at the end of the culture (FIG. 4G). The DNA concentration of the control culture increased sharply after 20 h post-induction reaching 1140 mg/l towards the end of the process. PEI very effectively reduced the amount of DNA in the culture supernatant keeping it to levels below or around 200 mg/l (FIG. 4D). In FIG. 4H it is readily apparent that the addition of PEI changed the balance between product and DNA in the culture supernatant. The lines of the PEI treated cultures are almost vertical to the x (DNA) axis as the DNA concentration remains stable during the fermentation while the product is being gradually released from the periplasm to the extracellular space. Therefore, PEI does not cause significant disruption of the cytoplasmic membrane, suggesting that the cells remain viable while becoming permeable allowing product to leak out to the extracellular space. This along with the very drastic removal of soluble DNA concentration allows earlier harvests and leads to broths where solids are easily separated by continuous-flow, pilot-scale centrifugation. It is possible that early release of the recombinant protein from the periplasm caused by PEI addition during cell culture will also reduce pressure on the host cell physiology.

Figure 5:
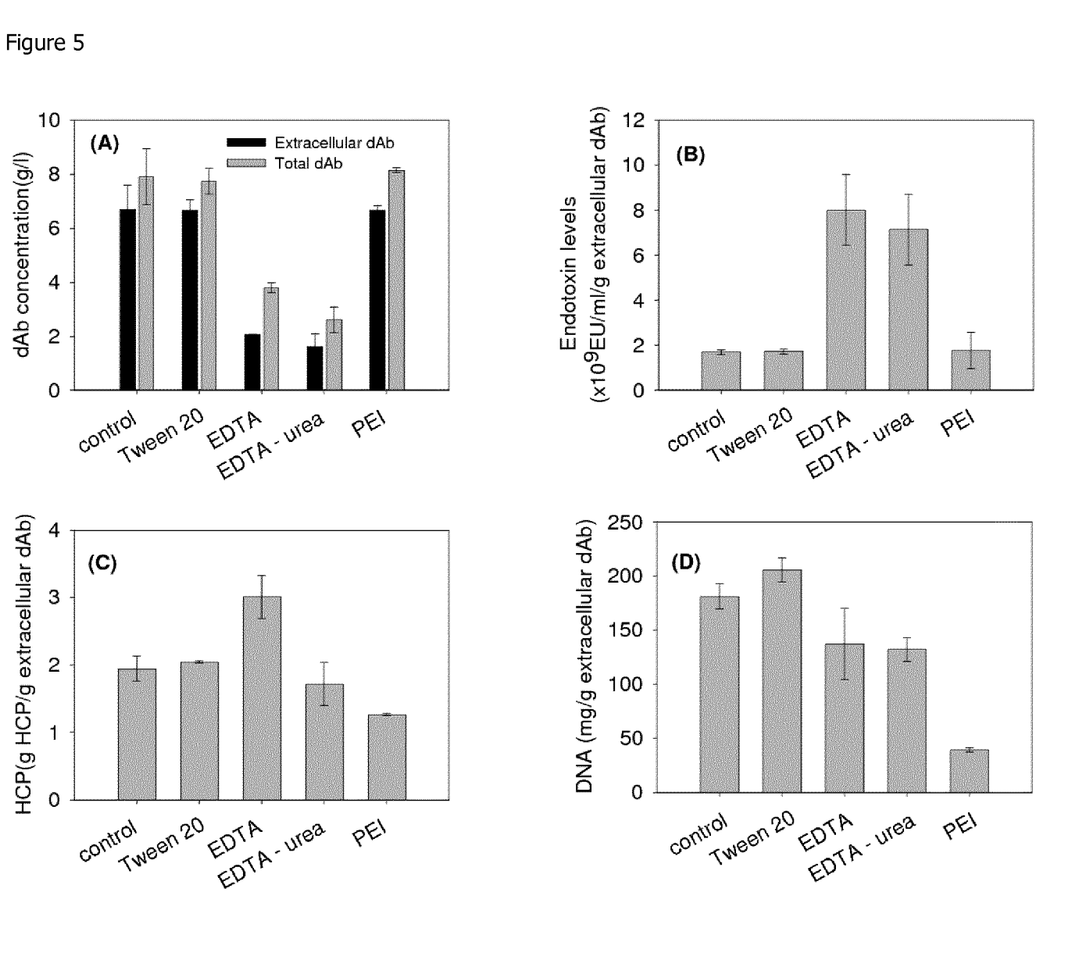
FIG. 5: Cell culture supplement impact on extracellular dAb and associated contaminants. All fermentations were carried out for 45 h post induction and reached a final cell density of ~25-30 g dwt/L. The supplements were applied as described in FIG. 4. 5A—Total dAb produced and extracellular dAb. The contaminant levels are compared with these extracellular dAb levels as a ratio in figures B-D. 5B—endotoxin; 5C—Host cell protein (HCP); 5D—DNA.

Example 7 Cell Culture Supplement Impact on Extracellular dAb and Associated Contaminants Extracellular dAb and total dAb yields are shown in FIG. 5A. Endotoxin, DNA, and HCP levels in the culture supernatant are important indicators of process related impurities and therefore product quality. Endotoxin is pyrogenic and must be kept below a predetermined minimum concentration in pharmaceutical products.

FIG. 5 summarises the performance of the various cell culture supplements used in FIGS. 3 and 4 in terms of the quality of the final broth obtained. The dAb concentration at harvest remains similar for the control culture, Tween™20 and PEI treated cultures while the EDTA and EDTA-urea have significantly lower both total and extracellular values (N3-fold). FIG. 5B shows a ~3-fold increase in endotoxin:extracellular dAb ratios for the EDTA and EDTA-urea cultures. The PEI treated cultures had endotoxin levels similar to the control and Tween™20 cultures. The HCP released or remaining in broth is not affected by Tween™ (compared with control) but is reduced ~2-fold for EDTA, ~3-fold for EDTA-urea and ~1.3 fold for PEI. FIG. 5C shows that HCP:extracellular dAb ratios were significantly higher for the EDTA but not the EDTA-urea treated cultures. PEI treated cultures exhibited decreased levels of HCP:extracellular dAb ratio which can either be attributed to lower cell lysis during the PEI treatment or to precipitation of some of these proteins by the polycation. Finally soluble DNA in the fermentation broth is ~5-fold lower for the PEI culture compared to control and Tween™20 cultures. EDTA and EDTA-urea treated cultures exhibited marginally lower DNA:extracellular dAb ratios due to extracellular dAb being 3-fold lower.

Example 8: 25 kDa Branched PEI

Experiments using 25 kDa branched PEI did not show the same effects as the 750 kDa branched PEI. This may have been due the 25 kDa PEI interfering with the protein affinity method for purification of the protein. The 25 kDa PEI appeared to be more toxic to the cells than the 750 kDa form. The respiration data show that after the onset of the PEI treatment both oxygen consumption rate and carbon dioxide evolution rate were decreased more rapidly than when the 750 kDa PEI was applied, signifying that the cells were dying. Accordingly, the cells died at an earlier stage and as a result less product was produced and almost all the product in the supernatant was probably due to cell lysis rather than cell permeabilisation. Therefore it was concluded that one should screen PEI variants via approaches as described herein to identify which formats and concentrations (eg feed rates via continuous addition, or bulk addition) are more preferred.

Example 9: Use of PEI with Other Antigen Binding Proteins

We confirm that the PEI fermentation strategy can be applied to more than one recombinant protein and it is not construct (e.g. vector or cell line) or product specific. Antigen binding proteins 2, 3 and 4 which bind to 3 different antigens (also different to DOM0101), with approximate MW of 25, 14 and 17 kDa respectively were treated with low feed addition of PEI (0.09 g/l/h) as described in Example 6. Samples for titre and soluble DNA concentration were withdrawn 5, 25 h and 50 h after the onset of PEI treatment.

Figure 6:
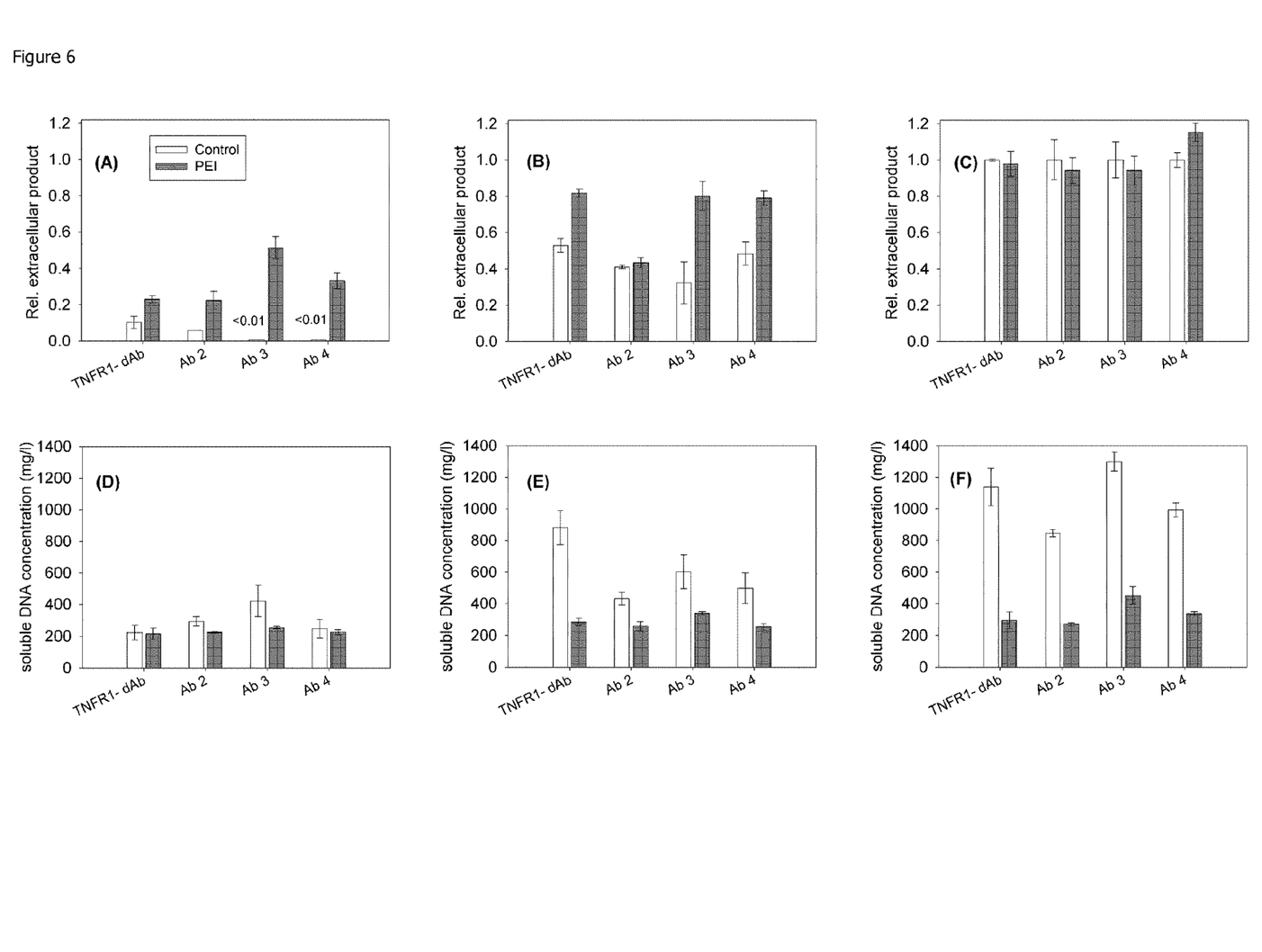

FIG. 6 indicates that PEI feed has an immediate positive effect on extracellular product. In all cases the extracellular product of the control cultures eventually catches up with the treated cultures. The 'heavier' antigen binding protein product Ab2 appears to be less preferentially released as time after PEI addition passes. However, the combinatorial increase in extracellular product titre and the efficient maintenance of extracellular soluble DNA to levels well below the 600 mg/l which is the limit for efficient solids separation in the centrifugation stage, can lead to shorter processes with significantly enhanced cell culture qualities.

CONCLUSIONS FOR EXAMPLES

PEI appears to have little negative effect on the cell physiology and at the same time removes DNA from the culture making it less viscous. Additionally there is an earlier product release/secretion to the extracellular space suggesting membrane permeabilisation. Therefore, the addition of PEI as a feed or cell culture enhancer during recombinant protein production increases the extracellular product titre, reduces fermentation time, and lowers power input due to the lower viscosities during the fermentation. Furthermore the presence of PEI leads to reduced levels of soluble HCP compared to other cell culture supplements tested. The 750 kDa PEI treatment was effective in the treatment of four different recombinant proteins. In all case the PEI had a positive effect on the release of the product, the ratio of product to soluble DNA was enhanced, the final product titre was unchanged compared to the control and, when full release of the final protein was achieved, the level of soluble DNA remaining was well below the limit to yield harvest broths suitable for clarification by continuous centrifugation at manufacturing scale. Furthermore, the use of PEI at an early stage of the fermentation can reduce the length of the fermentation time and consequently reduce the cost of the bioprocess.

Sequence Listing

```
SEQ ID NO: 1:
Amino acid sequence of DOM0101
EVQLLESGGGLVQPGGSLRLSCAASGFTFAHETMVWVRQAPGKGLEWVSH

IPPDGQDPFYADSVKGRFTISRDNSKNTLYLQMNSLRAEDTAVYHCALLP

KRGPWFDYWGQGTLVTVSS

SEQ ID NO: 2:
DNA sequence of DOM0101 - (no signal sequence)
GAAGTACAACTGCTGGAGAGCGGTGGCGGCCTGGTTCAACCGGGTGGTTC

CCTGCGCCTGTCCTGTGCGGCATCTGGTTTCACCTTCGCACACGAAACCA

TGGTGTGGGTTCGCCAAGCTCCGGGCAAAGGCCTGGAATGGGTAAGCCAC

ATTCCTCCAGATGGCCAGGACCCATTCTATGCGGATTCCGTTAAGGGTCG

CTTTACCATTTCTCGTGATAACTCCAAAAACACCCTGTACCTGCAGATGA

ACTCCCTGCGCGCCGAGGATACTGCGGTGTACCATTGTGCGCTGCTGCCT

AAACGTGGCCCGTGGTTCGATTACTGGGGTCAGGGTACTCTGGTCACCGT

AAGCAGC

SEQ ID NO: 3:
Amino acid sequence of alanine extended DOM0101
EVQLLESGGGLVQPGGSLRLSCAASGFTFAHETMVWVRQAPGKGLEWVSH

IPPDGQDPFYADSVKGRFTISRDNSKNTLYLQMNSLRAEDTAVYHCALLP

KRGPWFDYWGQGTLVTVSSA

SEQ ID NO: 4:
DNA sequence of C-terminal alanine extended
DOM0101 - (no signal sequence)
GAAGTACAACTGCTGGAGAGCGGTGGCGGCCTGGTTCAACCGGGTGGTTC

CCTGCGCCTGTCCTGTGCGGCATCTGGTTTCACCTTCGCACACGAAACCA
```

-continued

TGGTGTGGGTTCGCCAAGCTCCGGGCAAAGGCCTGGAATGGGTAAGCCAC

ATTCCTCCAGATGGCCAGGACCCATTCTATGCGGATTCCGTTAAGGGTCG

CTTTACCATTTCTCGTGATAACTCCAAAAACACCCTGTACCTGCAGATGA

-continued

ACTCCCTGCGCGCCGAGGATACTGCGGTGTACCATTGTGCGCTGCTGCCT

AAACGTGGCCCGTGGTTCGATTACTGGGGTCAGGGTACTCTGGTCACCGT

AAGCAGCGCG

---

The invention claimed is:

1. A method of producing a recombinant protein in a host cell comprising providing a cell culture, inducing expression of the recombinant protein, adding polyethyleneimine to said cell culture, and harvesting the recombinant protein directly from an extracellular medium of the cell culture without pre-treatment of the cell culture by thermal, mechanical, or chemical lysis, thereby producing the recombinant protein, wherein polyethyleneimine is added at any point in time from induction of expression of the recombinant protein to 30 minutes prior to harvest.

2. The method according to claim 1, wherein the host cell or cell culture is a Gram-negative bacteria with a periplasm.

3. The method according to claim 2 wherein the Gram-negative bacteria is *Escherichia coli*.

4. The method according to claim 1, wherein polyethyleneimine is added 30 minutes prior to harvest.

5. The method according to claim 1, wherein polyethyleneimine is added at the time of induction of expression of the recombinant protein.

6. The method according to claim 1, wherein the polyethyleneimine is added continuously during cell culture.

7. The method according to claim 1, wherein the polyethyleneimine is branched.

8. The method according to claim 1, wherein the molecular weight of the polyethyleneimine is from 50-1000 kDa.

9. The method according to claim 8, wherein the molecular weight of the polyethyleneimine is about 750 kDa.

10. The method according to claim 1, wherein the recombinant protein (i) is an antigen binding protein; and/or (ii) has a Molecular Weight (MW) of 25 kDa or less.

11. The method according to claim 10, wherein the antigen binding protein is an antibody.

12. The method according to claim 10, wherein the antigen binding protein is a domain antibody (dAb).

13. The method according to claim 1, further comprising purifying the harvested recombinant protein.

14. The method according to claim 13, wherein purifying the harvested recombinant protein comprises one or more chromatography steps.

* * * * *

SEQUENCE LISTING

<160> NUMBER OF SEQ ID NOS: 4

<210> SEQ ID NO 1
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Asp Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
            85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 2
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 2
gaagtacaac tgctggagag cggtggcggc ctggttcaac cgggtggttc cctgcgcctg      60
tcctgtgcgg catctggttt caccttcgca cacgaaacca tggtgtgggt tcgccaagct     120
ccgggcaaag gcctggaatg ggtaagccac attcctccag atggccagga cccattctat     180
gcggattccg ttaagggtcg ctttaccatt tctcgtgata actccaaaaa caccctgtac     240
ctgcagatga actccctgcg cgccgaggat actgcggtgt accattgtgc gctgctgcct     300
aaacgtggcc cgtggttcga ttactggggt cagggtactc tggtcaccgt aagcagc       357

<210> SEQ ID NO 3
<211> LENGTH: 120
<212> TYPE: PRT
<213> ORGANISM: Artificial Sequence
<220> FEATURE:
<223> OTHER INFORMATION: Amino acid sequence identified using molecular
      biology techniques.

```
<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Asp Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr His Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser Ala
            115             120

<210> SEQ ID NO 4
<211> LENGTH: 360
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 4
gaagtacaac tgctggagag cggtggcggc ctggttcaac cgggtggttc cctgcgcctg      60
tcctgtgcgg catctggttt caccttcgca cacgaaacca tggtgtgggt tcgccaagct     120
ccgggcaaag gcctggaatg ggtaagccac attcctccag atggccagga cccattctat     180
gcggattccg ttaagggtcg ctttaccatt tctcgtgata actccaaaaa caccctgtac     240
ctgcagatga actccctgcg cgccgaggat actgcggtgt accattgtgc gctgctgcct     300
aaacgtggcc cgtggttcga ttactggggt cagggtactc tggtcaccgt aagcagcgcg     360
```